US007965779B2

(12) United States Patent
She et al.

(10) Patent No.: US 7,965,779 B2
(45) Date of Patent: Jun. 21, 2011

(54) LOW POWER, WAVELET-BASED SPIKE DETECTOR

(75) Inventors: Christy L. She, Allen, TX (US); John G. Harris, Gainesville, FL (US); Jose C. Principe, Gainesville, FL (US)

(73) Assignee: University of Florida Research Foundating, Inc., Gainesville, FL (US)

( * ) Notice: Subject to any disclaimer, the term of this patent is extended or adjusted under 35 U.S.C. 154(b) by 748 days.

(21) Appl. No.: 11/909,060

(22) PCT Filed: Mar. 17, 2006

(86) PCT No.: PCT/US2006/009750
§ 371 (c)(1),
(2), (4) Date: Mar. 19, 2008

(87) PCT Pub. No.: WO2007/081368
PCT Pub. Date: Jul. 19, 2007

(65) Prior Publication Data
US 2008/0247471 A1     Oct. 9, 2008

Related U.S. Application Data

(60) Provisional application No. 60/663,464, filed on Mar. 18, 2005.

(51) Int. Cl.
*H04B 14/04*     (2006.01)
(52) U.S. Cl. ................................. 375/242
(58) Field of Classification Search ........... 375/242, 375/350; 327/554, 94, 559, 557; 600/546, 600/48; 607/45, 59
See application file for complete search history.

(56) References Cited

U.S. PATENT DOCUMENTS

| 4,692,909 | A | 9/1987 | Gard et al. |
| 5,845,243 | A | 12/1998 | Smart et al. |
| 6,868,348 | B1 * | 3/2005 | Stoutenburg et al. ........... 702/56 |
| 2005/0090756 | A1 * | 4/2005 | Wolf et al. ..................... 600/546 |
| 2006/0200035 | A1 | 9/2006 | Ricci et al. |

OTHER PUBLICATIONS

Rogers et al, An analog VLSI implementation of a multi-scale spike detection algorithm for extracellular neural recordings, Neural Eng., Conference Proceedings. 2nd Int'l IEEE EMBS Conference, Mar. 16-19, 2005, pp. 213-216.

Jui-Kuo Juan et al., Locally recurrent networks with multiple time-scales, Intl. Work. on Neural Networks for Signal Processing, vol. , No. , pp. 645-653, Sep. 1997.

Gosselin et al., Low-power implantable microsystem intended to multichannel cortical recording, Circuits and Systems, Proceedings of the 2004 International Symposium, Vancouver, BC, Canada, vol. 4, May 23-26, 2004, pp. 5-8.

(Continued)

*Primary Examiner* — Khai Tran
(74) *Attorney, Agent, or Firm* — Thomas, Kayden, Horstemeyer & Risley, LLP

(57) ABSTRACT

A multi-scale spike detector for performing multi-resolution spike detections of a signal is provided. The spike detector includes a gamma filter having cascaded low-pass filters. The cascaded filters collectively provide different cutoff frequencies, each of the filters having a respective output. One of the filters has an input, at which the signal is received. The spike detector further includes combining circuitry that combines at least some of the respective outputs of the cascaded filters. The differences formed from this combining provide a waveform representation of the input signal. The waveform representation consists essentially of spikes that occur in the signal.

16 Claims, 5 Drawing Sheets

OTHER PUBLICATIONS

The International Search Report and Written Opinion dated Apr. 9, 2007.

Rogers, et al., "An Analog VLSI Implementation of a Multi-Scale Spike Detection Algorithm for Extracellular Neural Recordings," Neural Engineering, 2005, Conference Proceedings, 2nd International IEEE EMBS Conference in Arlington, VA, Mar. 16-19, 2005 pp. 213-216.

Gosselin, et al., "Low-Power Implantable Microsystem Intended to Multichannel Cortical Recording," Circuits and Systems, 2004 Proceedings of the 2004 International Symposium in Vancouver, BC May 23-26, 2004, pp. 5-8.

Juan, et al., "Locally Recurrent Networks with Multiple Time-Scales" Neural Networks for Signal Processing Y1997 VII Proceedings of the 1997 IEEE Workshop Amelia Island, FL, Sep. 24-26, pp. 645-653.

Lewicki, "A Review of Methods for Spike Sorting: The Detection and Classification of Neural Action Potentials," Computation and Neural Systems, vol. 9, pp. R53-R78, 1998.

Nenadic, et al., "Spike Detection Using the Continuous Wavelet Transform" IEEE Transactions on Biomedical Engineering. vol. 52, No. 1, pp. 74-87, Jan. 2005.

Rogers, et al., "A Low-Power Analog Spike Detector for Extracellular Neural Recordings" Int'l Conf. IEEE Electronics, Circuits and Systems, Tel-Aviv, Israel Dec. 2004.

Chen, et al., An Analog VLSI Circuit Implementing an Orthogonal Continuous Wavelet Transform, IEEE Int. Conf. on Electronics, Circuits and Systems, vol. 2, Sep. 1998.

* cited by examiner

FIGS. 4(a)-(f)

LOW POWER, WAVELET-BASED SPIKE DETECTOR

CROSS-REFERENCE TO RELATED APPLICATIONS

This application is a §371 national stage entry of International Application No. PCT/US2006/009750, filed Mar. 17, 2006, which claims priority to U.S. Provisional Application No. 60/663,464, filed Mar. 18, 2005, both of which are hereby incorporated by reference.

STATEMENT REGARDING FEDERALLY SPONSORED RESEARCH OR DEVELOPMENT

This invention was made with government support under agreement N66001-02-C-8022 awarded by the Defense Advanced Research Projects Agency (DARPA). The Government has certain rights in the invention.

FIELD OF THE INVENTION

The invention is related to the field of electronic signal processing, and, more particularly, to devices and methods for processing spike trains.

BACKGROUND

An important aspect of technology and research related to sensory neurophysiology is the detection and analysis of neural signals. Neural signals are electrical signals from neurons in a neural network. With current technology, recordings have been made of electrical signals from neurons in neural networks such as cell cultures, hippocampal slices, in vivo tissue, and even the human brain. For example, to acquire signals from different neurons in a region of the brain, one or more electrode sensors can be positioned in a subject's brain for recording action potential arrival, times in neurons or nerve cells resulting from spontaneous or stimulus-evoked activity.

Of particular importance in many neurophysiology applications is the analysis of spike trains, which reflect the "firing" of neurons. A spike in this context can be broadly defined as a sharp transient that is visibly different from background noise. A specific application is the brain-machine interface, which must extract information from neural recordings collected in the motor cortex of a brain with the intended goal of creating predictive models for hand movement or direct control of a robotic device.

Currently available instruments and surgical procedures allow for such recordings from hundreds of electrodes at once. However, a yet unresolved problem is how to mitigate the resulting bottleneck that occurs when transfer is attempted of large bandwidth data streams, such as each channel being sampled at 25 kHz, 16 bits, without requiring that a subject be tethered with wires extending from one or more electrodes and connecting to a signal processing unit.

Conventional as well as more-recently proposed spike detection techniques typically suffer from shortcomings that preclude their use in low-power, stand-alone devices of sufficiently small size for implanting in a subject. Amplitude thresholding, for example, usually does not perform adequately since the signal-to-noise ratio (SNR) during detection typically drops. The technique also has been shown generally to lack robustness to DC shifts.

Both template matching and matched filtering, although sometimes providing reasonably accurate spike detection, typically require intensive computations and stable templates. These conventional techniques typically require hardware implementations that are not easily reduced to a size that is feasible for implantation in a subject. Similarly, a traditional wavelet technique, though performing well for real-time analyses, typically consumes too much power to be rendered in an implantable device.

SUMMARY OF THE INVENTION

The present invention provides a low-power, wavelet-based spike detector that, in the context of spike train analysis, enables the effective and efficient transfer of large bandwidth data streams. More particularly, the present invention enables a separate threshold to be set for each frequency band associated with a signal. The separate, multiple thresholds allow for enhanced overall performance over a wide variety of spike widths. The multi-resolution approach preferably effected by the present invention is applicable to a wide variety of signals, being especially advantageous for those signals characterized by sparse occurrences of spikes, such as neural signals.

One embodiment of the present invention is a multi-scale spike detector for performing multi-resolution spike detections of a signal. The spike detector can include a gamma filter comprising a cascaded plurality of low-pass filters, each of the filters providing a respective output "tap". A standard gamma filter is a cascade of low pass filters, where all filters have the same time constant. In a preferred embodiment, the gamma filter is a multiscale gamma filter which varies the time constant exponentially along the line of filters. However, since the spread of spike widths is generally only one order of magnitude, a standard gamma filter may be used with the invention.

Thus, in a preferred embodiment, the plurality of filters can collectively provide different cutoff frequencies. A first filter among the plurality of filters has an input at which a signal for which spike detection is to be performed is received.

In a preferred embodiment, moreover, an operational transconductance amplifier (OTA) and capacitor forms each low-pass filter. The OTA can be made with as few as five (5) transistors, preferably being CMOS transistors, which enables operation at very low power. Operation of the CMOS transistors at sub-threshold further reduces power consumption. Low power consumption is important in embedded applications, such as for implantation in a subject.

However, low pass filters to implement the cascaded plurality of low-pass filters can be embodied by equivalent low-pass filters in any technology to achieve the same effect. For example, switched capacitor filters, op amp filters, or current-mode filters can also be used with the invention. However, operational amplifiers require more transistors and larger power consumption. Other low pass filter embodiments require larger areas and/or higher power consumption as compared to the preferred OTA embodiment described above. Accordingly, throughout this application the filters will be described as comprising the preferred OTA and capacitor, with the understanding that the invention is not limited to this low pass filter arrangement.

The spike detector further includes combining circuitry. The combining circuitry can combine a plurality of the respective outputs of the plurality of filters. In a preferred embodiment, differences are taken between neighboring taps of the cascade of low-pass filters to achieve a bandpass filter bank. The differences formed from the combining can provide a waveform representation of the input signal. The waveform representation can consist essentially of spikes occurring in the signal. Thus, the output from the spike detector can be a binary pulse train.

Another embodiment of the present invention is a spike detecting system. The spike detecting system can include a substrate and a spike detector disposed on the substrate, thus providing an on-chip system for detecting spikes occurring in a signal. The spike detector includes a gamma filter, preferably being a multiscale gamma filter, and associated combining circuitry. The spike detecting system can further include a wireless transmitter for transmitting the binary pulse train provided by the spike detector to a remote location.

Yet another embodiment of the invention is a method for performing multi-resolution spike detections of a signal. The method can include determining a plurality of cutoff frequencies based upon frequencies of spikes detected, wherein the cutoff frequencies respectively define discrete frequency bands having corresponding thresholds. The method also can include determining the presence of at least one spike in each frequency band by comparing the signal to a threshold corresponding to each frequency band.

BRIEF DESCRIPTION OF THE DRAWINGS

There are shown in the drawings, embodiments which are presently preferred. It is to be understood, however, that the invention is not limited to the precise arrangements and instrumentalities illustrated.

DETAILED DESCRIPTION

The present invention effects a multi-resolution approach to spike detection. In general, spike detection is an advantageous data compression scheme for signals characterized by sparse occurrences of spikes, given that it involves just transmitting spike timing. Thus, it can be used to reduce the bandwidth of the data before data transmission via some selected medium. For data characterized by sparse occurrences of spikes, bandwidth can be reduced significantly by transmitting spike train binary pulse train information according to the invention.

More particularly, the present invention enables a separate threshold to be set for each frequency band associated with an input signal. The separate, multiple thresholds, as explained herein, allow for enhanced overall performance over a wide variety of spike widths. The multi-resolution approach effected by the present invention, though described herein primarily in the context of neural signals, will be recognized by those skilled in the art as having applicability to various types of signals, especially those characterized by sparse occurrences of spikes.

Figure 1:
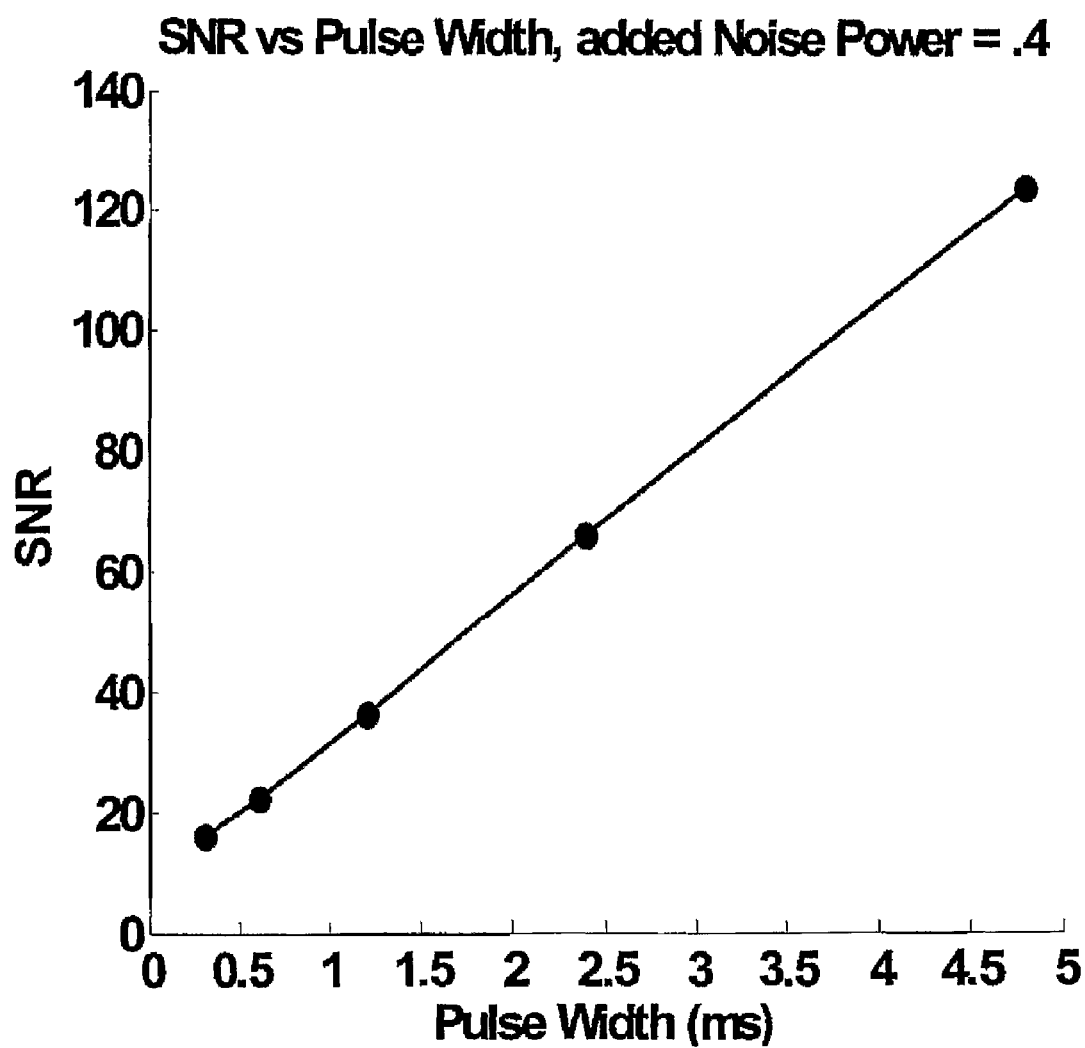
FIG. 1. is a plot of the SNR (dB) of a neural signal versus the pulse width (ms) of the signal.

For neural signals, the signal to noise ratio (SNR) associated with such signals not only varies from channel to channel and over time, but it also varies within each channel as a function of the width of the spike to be detected in the signal. FIG. 1 is a plot illustrating a linear relationship between the SNR of an exemplary neural signal and the pulse width of its associated spikes. As illustrated, typical neural spikes vary in width from 0.3 ms to about 5 ms. Because of this variability in the width of the typical neural spikes, a multi-resolution approach as provided by the present invention is helpful in improving performance of spike detection systems according to the invention in detecting spikes.

Moreover, the present invention provides an effective and efficient spike detector for accomplishing multi-resolution spike detection. The spike detector, more particularly, is characterized by ultra-low power consumption and robust small area analog circuitry, which makes it well-suited for a small-sized implantable device. The spike detector, as explained herein, provides a wavelet representation of a signal such as a neural signal. As will be readily understood by one of ordinary skill in the art, a wavelet can be defined by a mathematical function and can correspond to a waveform that is bounded in both frequency and duration. Wavelet transforms provide an alternative to more traditional Fourier transforms used for analyzing waveforms.

Figure 2:
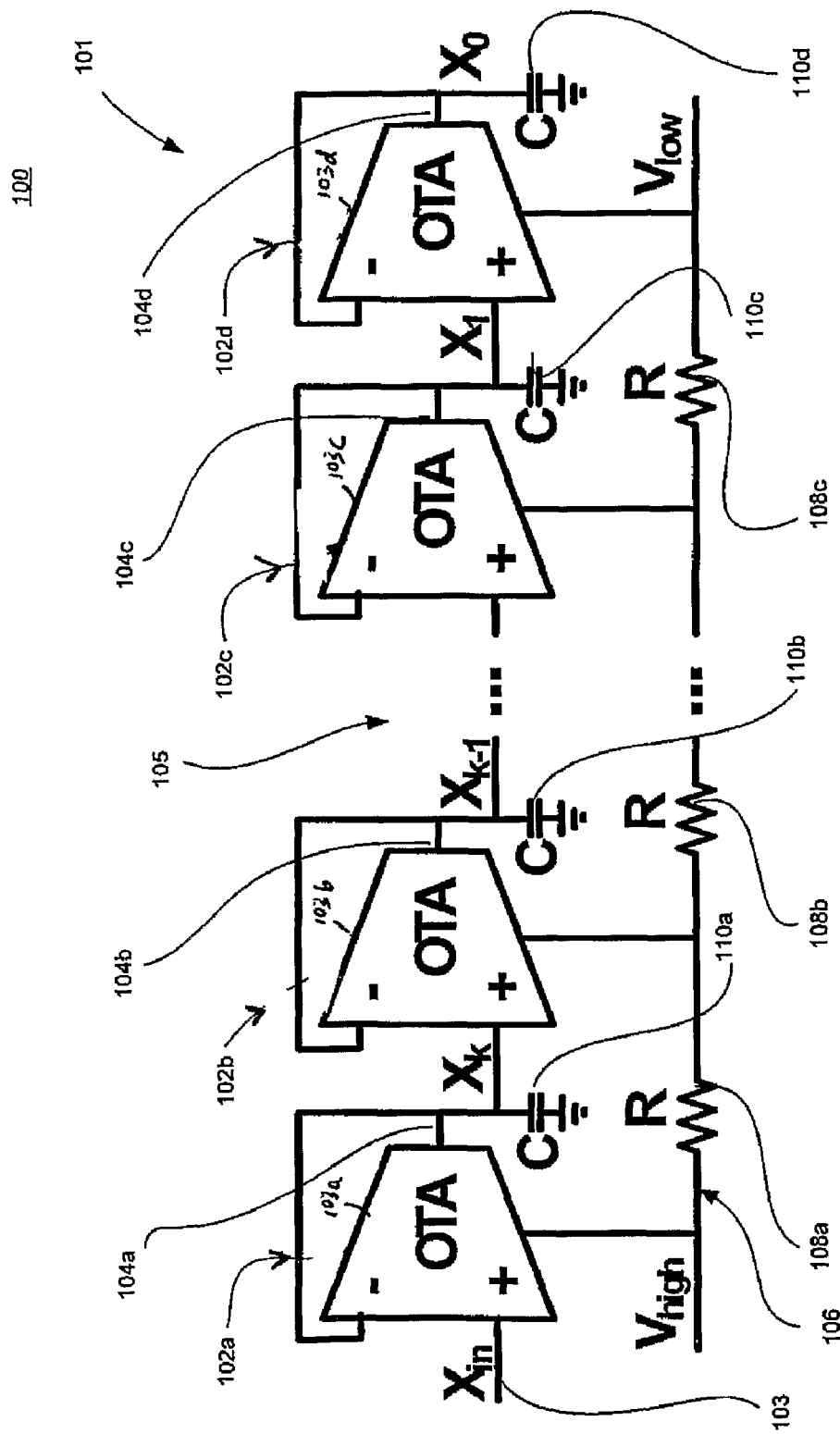
FIG. 2 is a schematic diagram of a multi-scale spike detector for performing multi-resolution spike detections of a signal, according to one embodiment of the present invention.

FIG. 2 is a schematic diagram of a multi-scale spike detector 100 for performing multi-resolution spike detections of a signal such as a neural signal, according to one embodiment of the present invention. The spike detector 100 illustratively includes a gamma filter 101. Gamma filter 101 is preferably a multiscale gamma filter. As illustrated, the gamma filter 101 comprises a cascaded plurality of low-pass filters $102a$-$102d$ which comprise OTAs $103a$-$103d$ together with respective associated capacitors $110a$-$110d$. Although only four (4) filters are shown, gamma filter 101 generally comprises more than four filters $102a$-$102d$, but can also comprise less than four filters. Although power rails are not shown, each OTA $103a$-$103d$ is supplied a power supply voltage, being the power rails of the chip, such as 0 and 5V.

As will be familiar to one of ordinary skill in the art, a low pass filter is a filter that passes only low frequencies. An important property of a low pass filter is its cutoff frequency, a term further employed below. By convention, this is the point in the frequency range at which the filter reduces the signal to −3 decibels (dB) of its original power. Spectral components that are attenuated below the cutoff of a filter are said to be in the stop band of a filter. Those above the half-power point are said to be in the pass band of the filter.

Illustratively, each of the low-pass filters $102a$-$102d$ of the gamma filter 101 comprises an operational transconductance amplifier (OTA) $103a$-$103d$ having a non-inverting and inverting inputs as well as a capacitor (C) $110a$-$110d$ that connects between the output of the OTAs and ground. As noted above, OTAs $103a$-$103d$ preferably comprise CMOS transistors operated in the sub-threshold condition, using as few as five (5) CMOS transistors. The inverting input is typically 180 degrees out-of-phase with the output of the OTA. As illustrated, each of the low-pass filters $102a$-$102d$ includes a feedback from the output of the OTA $103a$-$103d$ to the inverting input of the OTA.

As noted above, it is to be understood that the OTA and capacitor configuration of the low-pass filters $102a$-$102d$ is merely representative of the different types of filters that can be used to effect the gamma filter 101 of the present invention. Other types of filters, provided they exhibit the particular characteristics described below, can alternatively be utilized in constructing the gamma filter 101.

The plurality of filters 102a-102d collectively provide different cutoff frequencies. Each of the filters 102a-102d, as shown, has a respective output 104a-104d. The filter 102a that is illustratively first among the plurality of filters 102a-102d, moreover, has an input 103 for receiving from an external source, such as an embedded electrode, the signal that is multi-resolution spike detected by the spike detector 100. As illustrated, the input 103 for the signal corresponds to the input of the OTA.

As further illustrated, the spike detector also comprises combining circuitry 105. The combining circuitry combines a plurality of respective outputs 104a, 104b and 104c, 104d of the plurality of filters 102a-102d. The differences formed from this combining with the combining circuitry 105, as explained more particularly below, provide a waveform representation of the input signal, the waveform representation consisting essentially of spike occurrences in the signal as a binary pulse train.

Multi-resolution spike detection requires signal processing with localization in both the time and frequency domains. Illustratively, this achieved with the spike detector 100 being implemented with constant-Q filters, where Q represents a ratio of the center frequency of a filter to the width of the spectrum of the filter. Accordingly, for a filter to satisfy the requirement of a constant-Q filter, this ratio must remain essentially constant.

This condition is met and maintained by the spike detector 100. Firstly, each of the filters 102a-102d can have a different cutoff frequency. Secondly, the cutoff frequencies can be evenly spaced apart as measured on a log scale such that a ratio between a center frequency of each filter and a spectrum width of the filter is constant.

According to one embodiment, to achieve these conditions, OTAs 103a-103d are biased differently using different bias voltages. For example, resistive line 106 which forms a simple voltage divider has various taps which are connected to each of the filters 102a-102d. The resistive line 106 supplies to each of the filters a different, respective bias voltage. The bias voltages preferably vary linearly; that is, the difference between the bias voltages of any pair of the filters 102a-102d is an integer multiple of the difference between the bias voltage of any other pair of the filters. The bias voltage sets the cutoff frequency each low-pass filter. If the CMOS transistors comprising each OTA 103a-103d of the filters 102a-102d are operated in their subthreshold region, then linear differences in the bias voltages of the respective filters creates an exponential change in a corresponding bias current. The exponential change in current allows the cutoff frequencies of each filter to be substantially evenly spaced on the log scale, as described above, and each accordingly exhibits the constant-Q condition defined above.

In the present context, the running of an OTA in its subthreshold region refers to a phenomenon associated with the MOS transistors that comprise OTAs according to the invention. In a MOS transistor, the amount of current flowing from a source to a drain is controlled by an electric field induced by an applied voltage at the transistor's gate, as will be readily understood by one of ordinary skill in the art. The electric field attracts charge carriers from either side of the channel at the source and the drain, forming a thin conductive layer between each. Higher voltage induces a stronger electric field that, in turn, causes more current to flow through the transistor.

The underlying semiconductor physics is such that there are two modes by which current flows through the transistor: diffusion, the natural flow of particles from regions of low concentration to regions of higher concentration, and drift, the flow of particles under the influence of an applied force. In the present context, MOS transistors, and hence the OTAs that comprise such transistors, operate in the subthreshold region when the flow of current from source to drain is due to diffusion. In this mode of operation, the MOS transistors and amplifiers are said to be operating in their subthreshold region.

The spike detector 100 generates a wavelet representation for a received signal, where as noted above a wavelet denotes a mathematical function and corresponds to a waveform that is bounded in frequency and duration. According to one embodiment, the differences formed from the combining effected by the combining circuitry 105 are the differences between the respective outputs 104a-104d (corresponding to the respective taps of each OTA) of each set of neighboring or adjacent filters 102a-102d. More generally, for a N-stage gamma filter, the combining circuitry yields differences $X_k - X_{k-1}$ corresponding to each pair of outputs 104a-104d at the kth stage, where k varies from 1 to N. The functional result is thresholded bandpass filters that determine the presence of a spike at one of a number of different scales corresponding to the different cutoff frequencies.

Figure 3:
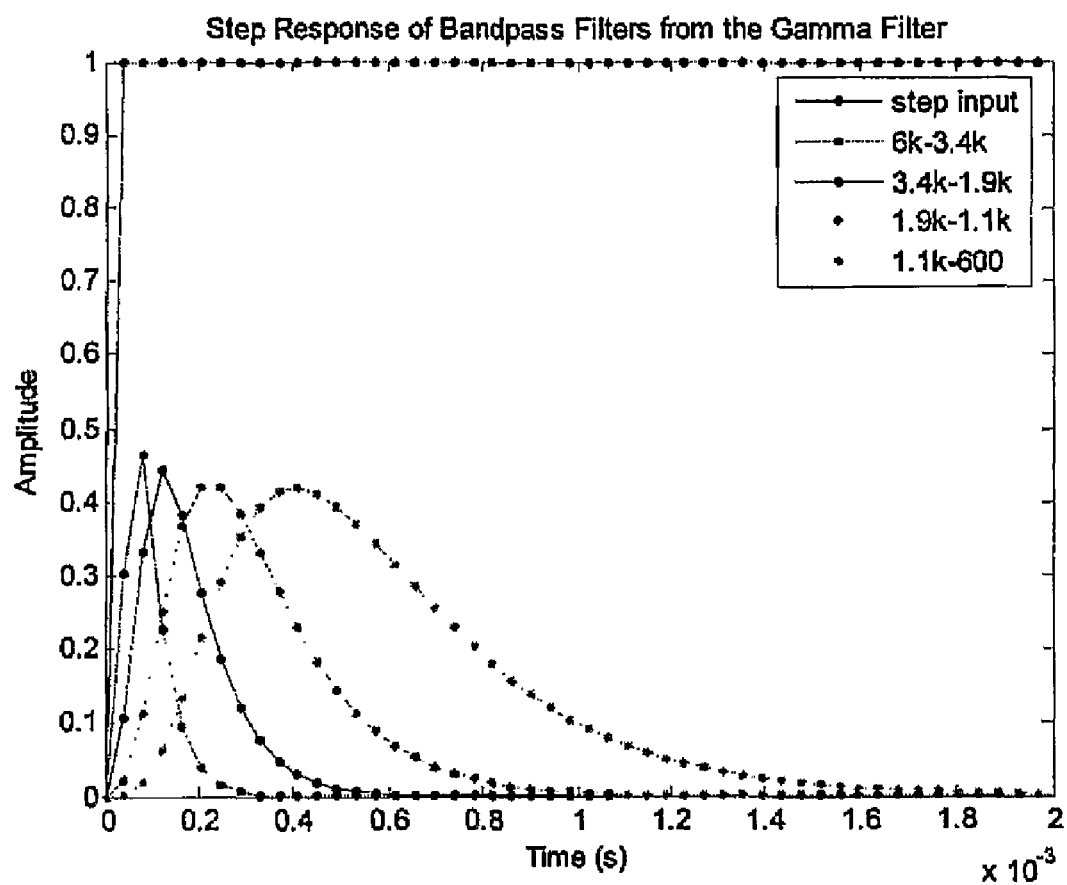
FIG. 3 is a plot of the amplitudes of step responses of resulting bandpass filters effected with a multiscale gamma filter versus time (ms), according to another embodiment of the present invention.

The outputs at each scale are preferably ORed with one another after appropriate compensation for varying delays. The delay at each scale is determined from the step response delay for each resulting bandpass filters, as illustrated in FIG. 3. The combination starts with the lowest frequency scale being shifted in time to account for an additional delay from the second lowest frequency scale. Then, the two scales are ORed. Alternatively, however, instead of ORing the scales together, binary values for each scale alternatively can be determined and used in conjunction with a spike sorting algorithm It is important to mitigate the risk that a spike will not be detected twice. In order to reduce the risk of spurious detections, a small minimum distance criterion is enforced algorithmically at each scale. If the minimum distance is not met, a latter spike time is removed. Subsequently, the new combined scale is combined with the next lowest frequency scale. This continues until there is only one output scale left.

Figure 4:
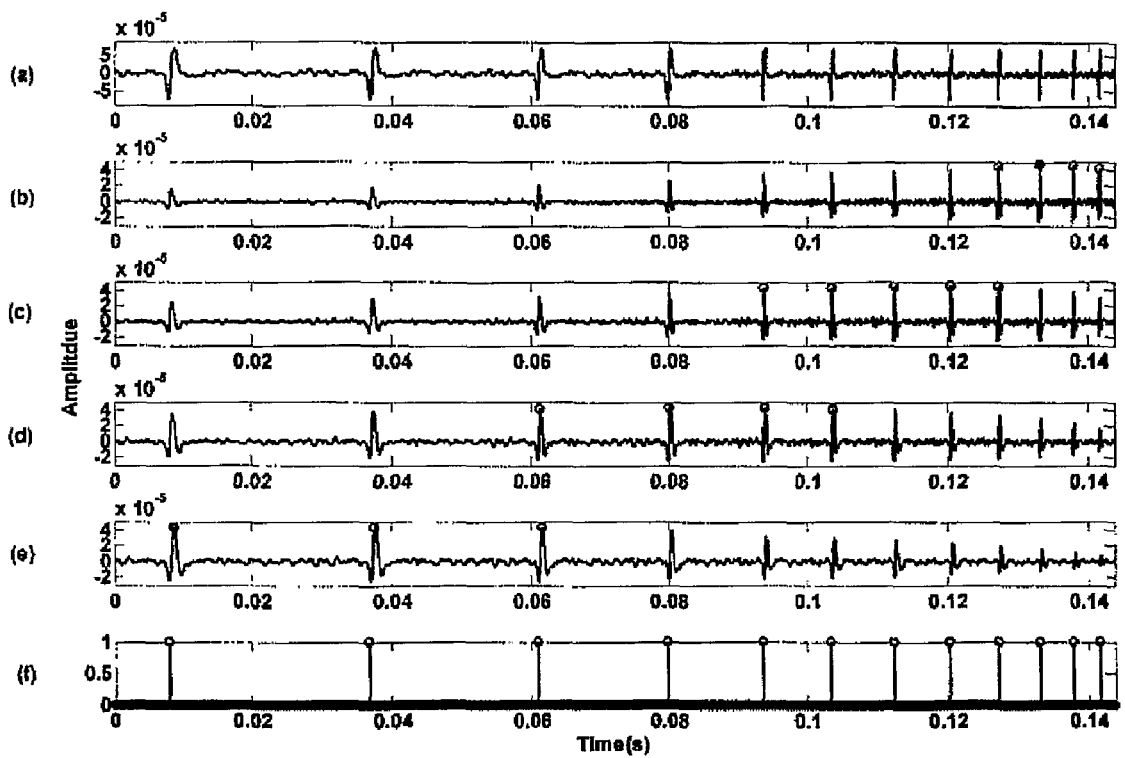
FIGS. 4(a)-(f) are plots of amplitudes for different scales and for a combined scale, according to yet another embodiment of the present invention.

FIGS. 4(a)-(f) illustrate the outputs from each scale for several spike widths as well as their final combined output. FIG. 4(a) shows the concatenated input signal with spikes widths starting at 3 ms and going as small as 0.3 ms. FIG. 4(b) shows a 6 k-3.4 k Hz bandpass filtered signal and the detected spike from this scale. FIG. 4(c) shows a 3.4 k-1.9 k Hz bandpass filtered signal and the detected spike from this scale. FIG. 4(d) shows a 1.9 k-1.1 k Hz bandpass filtered signal and the detected spike from this scale. FIG. 4(e) shows a 1.1 k-600 Hz bandpass filtered signal and the detected spike from this scale. FIG. 4(f) shows a combined output from each scale, which is the final output of the multi-scale spike detector 100.

The input contained twelve spikes with very little noise whose widths encompassed the typical spike range of 0.3 to 3 ms. As noted above, the beginning of the waveform starts with the widest spike, such as 3 ms, and ends with the narrowest. It thus can be seen that the narrow spikes are better detected with the high frequency bands and the wider spikes are better detected with the low frequency bands. It should be noted that while for the very high SNR input the middle frequency band could detect all of the spikes if the threshold was set low enough, in the usual case of lower SNR this would not be possible.

Setting thresholds by hand is cumbersome for a large number of channels. For the multi-scale algorithm each scale's threshold would have to be set independently. This could hinder finding optimal threshold levels for an algorithm to work most efficiently. In ideal cases where the pdfs of the signals are Gaussian, or normally, distributed and share the same known variance, the Bayes' detector provides the optimal threshold assuming, that the costs of false detections and missed detections are weighted equally. In this Bayes' equation following, $\sigma^2$ represents the variance, $\mu$ the mean, $P_0$ the probability of noise, and $P_1$ the probability of a spike plus noise:

$$\lambda = \sigma_0^2 \frac{\ln\left(\frac{P_0}{P_1}\right)}{\mu_1 - \mu_0} + \frac{\mu_1 + \mu_0}{2}$$

Using the Bayes' equation, the threshold of each scale can be related to each other so that setting one threshold automatically sets the rest. One option is to allow raw segments of each channel to be periodically sent out so that the parameters can be adjusted for the circuit periodically. This could mean that each channel takes turns having its raw data transmitted while the rest of the channels only send their detected spikes so that the overall transmission bandwidth limitations are still met.

Figure 5:
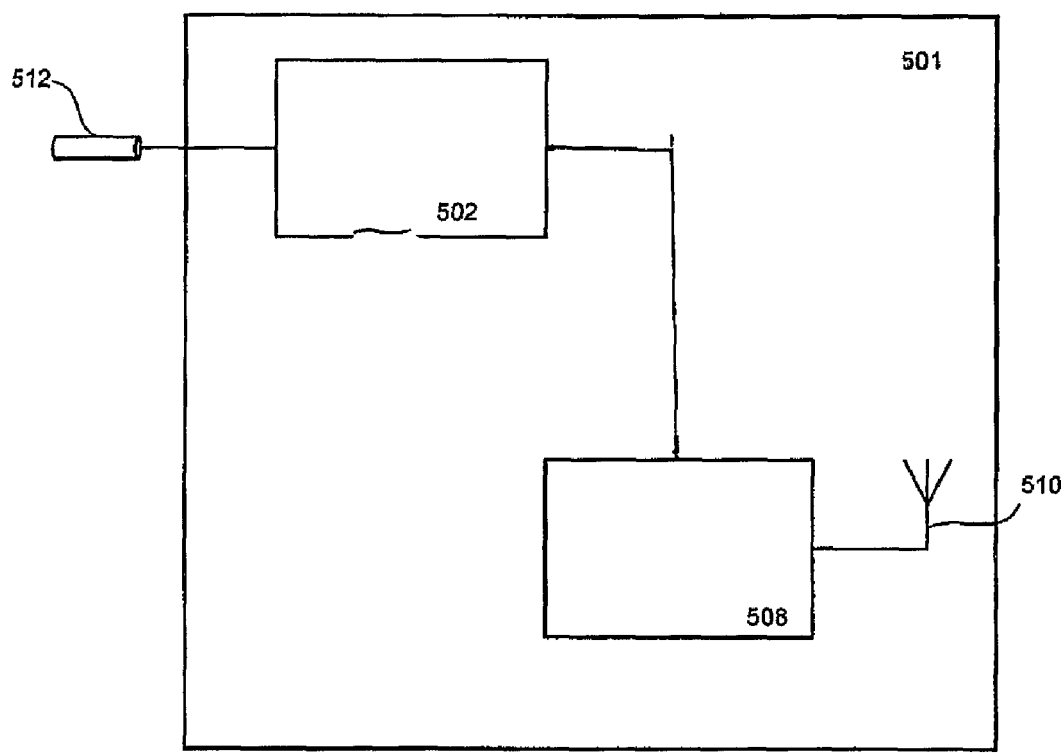
FIG. 5 is a schematic diagram of an on-chip spike detecting device, according to still another embodiment of the present invention.

Among the advantages of the spike detector 100 is that in implementing the underlying multi-resolution approach of the invention, the spike detector itself can be implemented in a reduced size, low-power consumption device. Such a device is illustrated in FIG. 5, which is a schematic diagram of a spike detecting system 500 according to another embodiment of the invention.

The spike detecting system 500 can be characterized as an on-chip system that illustratively includes a substrate 501, such as a semiconductor (e.g. Si) substrate. A spike detector 502, as described above, is built on the substrate 501. The output of spike detector 502 is a binary pulse train. The output of spike detector 502 is connected to wireless transmitter 508, which is connected to an on-chip antenna 510. Although not explicitly shown, the spike detecting system 500 is powered by an on-chip power source (e.g. battery) also associated with the substrate 501.

As already noted, the spike detector 100 has applicability to various types of signals, particularly those characterized by sparse occurrences of spikes such as neural signals. Accordingly, the spike detecting system 500 can be sufficiently sized on a single chip so as to be implantable in, for example, the brain of a human or animal subject. Optionally, therefore, an implanted electrode 512 can be connected to the spike detector 502.

More particularly in this context, the electrode 512 can be implanted at various depths with a brain cortex to detect signals from neurons in the brain cortex. The detected signals from the neuron are conveyed via the electrode 512 to the on-chip spike detector 502, which performs multi-resolution spike detections on the neural signal in accordance with the techniques already described. The resulting output of the spike detector can be transmitted by the transmitter 508 via the on-chip antenna 510, which can be an RF antenna, for conveying the signal via an RF channel to an external monitor (not shown). The spike detecting system 500 optionally can include a multiplexer (also not shown) for multiplexing multiple signals from multiple electrodes that can connected through the multiplexer to the spike detector 502.

Yet another embodiment of the present invention is a method for performing multi-resolution spike detections of a signal, such as by using multi-scale gamma filters according to the invention. The method illustratively includes determining a plurality of cutoff frequencies based upon frequencies of spikes detected, wherein the cutoff frequencies respectively define discrete frequency bands with corresponding thresholds. The method further includes determining the presence of at least one spike in each frequency band by comparing the signal to a threshold corresponding each frequency band.

The invention can be realized in hardware, software, or a combination of hardware and software. The invention, moreover, can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The invention can be embodied in other forms without departing from the spirit or essential attributes thereof. Accordingly, reference should be made to the following claims, rather than to the foregoing specification, as indicating the scope of the invention.

We claim:

1. A multi-scale spike detector for performing multi-resolution spike detections of a signal, the spike detector comprising:
a gamma filter having a cascaded plurality of low-pass filters, each of said plurality of filters collectively providing different cutoff frequencies, and each of said plurality of filters having a respective output, and, wherein a first of said plurality of filters has an input, said signal being received at said input; and
combining circuitry combining a plurality of said respective outputs of said plurality of filters, wherein differences formed from said combining provide a waveform representation of said input signal, said waveform representation consisting essentially of spike occurrences in said signal.

2. The spike detector of claim 1, further comprising a resistive line connected to each of said filters, said resistive line supplying to each of said filters a respective bias voltage.

3. The spike detector of claim 2, wherein each bias voltage supplied to one of said filters is different from each other bias voltage supplied to each other of said filters.

4. The spike detector of claim 3, wherein said bias voltages vary linearly from one another.

5. The spike detector of claim 1, wherein each of said low-pass filters is biased by a respective bias voltage to have an exponentially varying cut-off frequency.

6. The spike detector of claim 5, wherein each of said filters has a different cutoff frequency.

7. The spike detector of claim 6, wherein said cutoff frequencies are evenly spaced on a log scale such that a ratio between a center frequency of each filter and a spectrum width of said filter is constant, said gamma filter thus being a constant-Q filter.

8. The spike detector of claim 7, wherein each of said filters comprises a low-pass operational transconductance amplifier (OTA).

9. The spike detector of claim 1, wherein said signal comprises a neural signal coupled to an implanted electrode in a brain of a subject, said implanted electrode being electrically connected to said input of said first filter.

10. A spike detecting system, comprising:
a substrate;
a spike detector disposed on said substrate, said spike detector comprising:
a gamma filter comprising a cascaded plurality of low-pass filters, said plurality of filters collectively providing different cutoff frequencies, each of said filters having a respective output, and a first of said plurality of filters having an input to receive a signal, and combining circuitry combining a plurality of said respective outputs of said plurality of filters, wherein differences formed from said combining provide a waveform representation of said input signal, said waveform representation consisting essentially of spike occurrences in said signal as a binary pulse train, and
a wireless transmitter connected to said spike detector for transmitting said binary pulse train.

11. The system of claim 10, further comprising an RF antenna connected to said transmitter.

12. The system of claim 10, further comprising a multiplexer (MUX) in electrical communication with said spike detector for multiplexing a plurality of signals from multiple electrodes.

13. The system of claim 12, wherein the signals comprise neural signals generated by a neural network.

14. The system of claim 13, wherein the plurality electrodes are connected to the neural network.

15. A method for performing multi-resolution spike detections of a signal, the method comprising:
determining a plurality of cutoff frequencies based upon frequencies of spikes detected wherein the cutoff frequencies respectively define discrete frequency bands with corresponding thresholds; and
determining the presence of at least one spike in each frequency band by comparing the signal to a threshold corresponding each frequency band.

16. The method of claim 15, and wherein differences between adjacent bands are thresholded separately.

* * * * *